(12) United States Patent
Lee et al.

(10) Patent No.: US 7,629,481 B2
(45) Date of Patent: *Dec. 8, 2009

(54) ANSA-METALLOCENE COMPOUND, PROCESS OF PREPARING THE SAME, AND PROCESS OF PREPARING POLYOLEFIN USING THE SAME

(75) Inventors: Choong Hoon Lee, Daejeon (KR); Jong Joo Ha, Daejeon (KR); Seung Whan Jung, Suwon (KR); Eunjung Lee, Daejeon (KR); Beomdoo Seo, Daejeon (KR); Young Whan Park, Daejeon (KR); Hyosun Lee, Daejeon (KR); Sung Don Hong, Daejeon (KR); Young Chul Won, Suwon (KR); Bun Yeoul Lee, Suwon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/234,504

(22) Filed: Sep. 23, 2005

(65) Prior Publication Data
US 2006/0069221 A1    Mar. 30, 2006

(30) Foreign Application Priority Data
Sep. 25, 2004    (KR)    ............. 10-2004-0077624

(51) Int. Cl.
*C07F 17/00* (2006.01)
*C08F 4/76* (2006.01)
*C08F 4/64* (2006.01)

(52) U.S. Cl. ............... 556/53; 556/52; 556/51; 526/943; 526/941; 526/160; 526/170

(58) Field of Classification Search ........... 526/160, 526/943, 170; 556/53, 52
See application file for complete search history.

(56) References Cited

U.S. PATENT DOCUMENTS

| 5,384,298 A | * | 1/1995 | Inahara et al. ............. 502/104 |
| 5,597,935 A | | 1/1997 | Jordan et al. |
| 5,631,202 A | * | 5/1997 | Ewen ..................... 502/117 |

(Continued)

FOREIGN PATENT DOCUMENTS

KR    P1998-025280    *    7/1998

(Continued)

OTHER PUBLICATIONS

Cho et al. Organometallics 2004, 23, 4693-4699; electronic version available Aug. 14, 2004.*

(Continued)

*Primary Examiner*—David Wu
*Assistant Examiner*—Rip A. Lee
(74) *Attorney, Agent, or Firm*—Cantor Colburn LLP (57) ABSTRACT

Provided are a bridged metallocene compound particularly suitable for copolymerization of ethylene and alpha-olefin or cyclic olefin, a process of preparing the metallocene compound, and a process of preparing polyolefin using the metallocene compound. The bridged metallocene compound has low steric hindrance and good (co)polymerization activity, and thus, exhibits good activity in copolymerization of ethylene and alpha-olefin such as 1-hexene or 1-octene. Furthermore, the process of preparing the bridged metallocene compound is simplified, and thus, suitable for mass production.

4 Claims, 2 Drawing Sheets

U.S. PATENT DOCUMENTS 5,650,471 A * 7/1997 Abe et al. .................. 526/160
5,892,081 A 4/1999 Suling et al.
6,162,935 A 12/2000 Chen et al.

FOREIGN PATENT DOCUMENTS

| | | |
|---|---|---|
| KR | 100398740 B1 | 9/2003 |
| TW | 218884 | 2/1992 |
| TW | 309523 | 7/1997 |
| TW | 523524 | 3/2003 |
| TW | 200401784 | 2/2004 |
| TW | 200413423 | 8/2004 |
| WO | 9613532 | 5/1996 |
| WO | 0009524 | 2/2000 |
| WO | WO 2004/020481 A1 * | 3/2004 |
| WO | 2004037839 A1 | 5/2004 |

OTHER PUBLICATIONS

P1998-025280 (abstract in English).*
Won et al. Synthesis 2004, 7, 1052-1056; electronic version available Feb. 4, 2004.*
"Syntheses of 2,5- Dimethylcyclopentadienyl ansa-Zirconocene Complexes and Their Reactivity for Ethylene/ Norbornene Copolymerization"; Authors: Eun Sook Cho, et al.; Organometallics, 23 (20), pp. 4693-4699 (2004).
Korean Intellectual Property Office Notice to Submit Response; Dated Feb. 1, 2006.
Preliminary Notice of the First Office Action with Search Report dated Apr. 25, 2008.
Cho, Eun Sook, et al., Synthesis of 2, 5-Dimethylcyclopentadienyl ansa-Zirconocene Complexes and Their Reactivity for Ethylene/ Norbornene Copolymerization, Organometallics, 2004, 23, pp. 4693-4699.

* cited by examiner

ANSA-METALLOCENE COMPOUND, PROCESS OF PREPARING THE SAME, AND PROCESS OF PREPARING POLYOLEFIN USING THE SAME

CROSS-REFERENCE TO RELATED PATENT APPLICATION

This application claims priority from Korean Patent Application No. 10-2004-0077624, filed on Sep. 25, 2004, in the Korean Intellectual Property Office, the disclosure of which is incorporated herein in its entirety by reference.

1. Field of the Invention

The present invention relates to an ansa-metallocene compound, and more particularly, to a metallocene compound suitable for copolymerization of ethylene and alpha-olefin or cyclic olefin, a process of preparing the metallocene compound, and a process of preparing polyolefin using the metallocene compound.

2. Description of the Related Art

A metallocene compound is a Group IV transition metal compound containing one or two cyclopentadienyl ligands, and can be used as a catalyst for olefin polymerization after being activated by methylaluminoxane or a boron compound. Such a metallocene catalyst has uniform active sites, and thus can produce a polymer in a narrow molecular weight distribution and provide easy copolymerization and uniform comonomer distribution. Furthermore, for propylene polymerization, the stereostructure of a polymer can be controlled according to the symmetry of the metallocene catalyst. In particular, unlike a conventional Ziegler-Natta catalyst capable of preparing only isotactic polypropylene, the metallocene catalyst can stereoregularly prepare various polypropylenes, including isotactic, syndiotactic, atactic, and hemiisotactic. For example, syndiotactic polypropylene synthesized using a metallocene catalyst has characteristics such as low crystallinity, appropriate strength and hardness, good transparency, and high impact resistance.

Owing to the development of such catalyst systems, many efforts have been made to develop catalysts suitable for producing copolymers of ethylene and alpha-olefin, such as linear low-density polyethylene (LLDPE), very low-density polyethylene (VLDPE), ethylene propylene monomer (EPM) copolymer, and ethylene-propylene diene monomer (EPDM) copolymer, cyclic olefin copolymers (COCS) of ethylene and cyclic olefin or alpha-olefin and cyclic olefin, and copolymers of ethylene, alpha-olefin, and styrene. Catalysts used to produce these copolymers must satisfy the following requirements: good activity, good reactivity with a comonomer, and uniform comonomer distribution.

Meanwhile, a metallocene catalyst is more expensive than a conventional Ziegler-Natta catalyst. Thus, the metallocene catalyst requires high activity in order to be cost effective. In particular, if the metallocene catalyst has high reactivity with a comonomer, a polymer containing a large ratio of the comonomer component can be obtained in spite of using a smaller amount of the comonomer.

Generally, it is known that a bridged catalyst has high reactivity with a comonomer. In detail, according to a study by F. J. Karol, to produce LLDPE with a density of 0.930 using 1-hexene as a comonomer, hexane and ethylene are used in a ratio of only 0.004-0.005 in the presence of a bridged catalyst but in a ratio of up to 0.02 in the presence of a non-bridged catalyst (1997. 4. 18. America Palm Coast, Fla., Polymer Reaction Engineering Foundation Conference).

Thus, bridged catalysts have received much interest for producing the above-mentioned copolymer. The bridged catalysts also have an advantage of controlling the molecular structure of a propylene polymer according to the molecular symmetry of the bridged catalysts. Bridged catalysts studied hitherto can be classified into three groups according to bridge type: (a) an ethylene-bridged catalyst in which two cyclopentadienyl ligands are connected by —(CH$_2$CH$_2$)—, (b) a silicon-bridged catalyst in which two cyclopentadienyl ligands are connected by —SiR$_2$—, and (c) a methylene-bridged catalyst in which two cyclopentadienyl ligands are connected by —CR$_2$—. The synthesis methods of these catalysts are schematically shown in reaction schemes below:

(a)

(b)

-continued (c)

The two cyclopentadienyl rings of each bridged catalyst may be unsubstituted or substituted by various types of substituents. However, it is impossible to synthesize a cyclopentadienyl ligand in which only the alpha position is substituted by a substituent using a conventional method. The reason can be explained as follows with reference to the above synthesis methods. A bridged catalyst can be typically synthesized by nucleophilic substitution of ethylenedibromide, dialkylsilicondichloride, or fulvene with a substituted cyclopentadienyl anion. In this case, the substituent of the cyclopentadienyl anion shifts to the beta position due to steric hindrance. If a 1,3-disubstituted cyclopentadienyl anion is used, a cyclopentadienyl ligand in which both the alpha and beta positions are substituted is produced but no cyclopentadienyl ligand in which only the alpha position is substituted is produced.

In a metallocene catalyst, an opposite side to the bridge, i.e., the beta position of cyclopentadienyl receives a monomer and allows for the growth of a polymer. Thus, a metallocene compound in which only the alpha position of cyclopentadienyl is substituted can easily receive a monomer with high steric hindrance, which enables easy copolymerization. Even though a bridged catalyst with no substituent has the smallest steric hindrance, it generally has low activity and cannot properly perform copolymerization. This is because an electron effect, together with steric hindrance, can also affect catalytic activity and degree of copolymerization. That is, a cyclopentadienyl ring substituted by an electron donor group, such as an alkyl group, can increase catalytic activity and a degree of copolymerization.

Korean Patent No. 398740 discloses a bridged metallocene catalyst in which only the alpha position is substituted by a substituent and a method of preparing the same. However, synthesis of 1,4-pentadiene, used as a starting material, is not cost effective, and a preparation method for the bridged metallocene catalyst using 1,4-pentadiene must be performed under high temperature and pressure and requires a large number of reaction processes, which renders mass production of the catalyst difficult. Furthermore, since all the alpha positions of the two cyclopentadienyl ligands are substituted by substituents, the catalyst exhibits low activity for copolymerization of ethylene and alpha-olefin due to steric hindrance.

SUMMARY OF THE INVENTION

The present invention provides an ansa-metallocene compound with low steric hindrance and good (co)polymerization activity.

The present invention also provides a process of preparing the metallocene compound.

The present invention also provides a process of preparing polyolefin using the metallocene compound.

According to an aspect of the present invention, there is provided a bridged metallocene compound represented by Formula 1 below:

(1)

wherein $R_1$, $R_2$, $R_3$ and $R_4$ are each independently a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, provided that $R_1$ and $R_2$ are not hydrogen at the same time, and $R_3$ and $R_4$ may be connected by an alkylidyne radical containing an alkyl moiety of 1-20 carbon atoms or an aryl moiety of 6-20 carbon atoms to form a ring; $Q_1$ and $Q_2$ are each independently a halogen atom, an alkyl group of 1-20 carbon atoms, an alkenyl group of 2-10 carbon atoms, an alkylaryl group of 7-40 carbon atoms, an arylalkyl group of 7-40 carbon atoms, an aryl group of 6-20 carbon atoms, a substituted or unsubstituted alkylidene group of 1-20 carbon atoms, a substituted or unsubstituted amino group, an alkylalkoxy group of 2-20 carbon atoms, or an arylalkoxy group of 7-40 carbon atoms; B is a carbon, silicon, germanium, phosphorus, or nitrogen atom; and M is a Group IV transition metal.

According to another aspect of the present invention, there is provided a process of preparing a bridged metallocene compound represented by Formula 5 below, the method including:

a) reacting a compound of Formula 3 below with a compound of Formula 2 below treated with a lithium salt or a Grignard reagent, followed by acid treatment, to prepare a compound of Formula 4 below; and b) treating the compound of Formula 4 with a lithium salt and reacting the reaction product with a Group IV metal-containing salt:

(2)

(3)

(4)

(5)

wherein $R_1$, $R_2$, $R_3$, $R_4$, M, X, $Q_1$ and $Q_2$ are as defined in Formula 1; $R_5$ is an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylakyl group of 7-40 carbon atoms, an arylalkenyl group of 8-40 carbon atoms, an alkynyl group of 2-10 carbon atoms, or a hydrocarbyl-substituted Group XIV metalloid radical; and X is a halogen atom.

According to still another aspect of the present invention, there is provided a process of preparing a bridged metallocene compound represented by Formula 9 below, the process including:

a) reacting a compound of Formula 6 below with a compound of Formula 2 below treated with a lithium salt or a Grignard reagent;

b) reacting the reaction product of a) with a compound of Formula 7 below, followed by acid treatment, to prepare a compound of Formula 8 below; and c) treating the compound of Formula 8 with a lithium salt and reacting the reaction product with a Group IV metal-containing salt:

(2)

-continued (6)

(7)

(8)

(9)

wherein $R_1$, $R_2$, $R_3$, $R_4$, $R_5$, X, M, $Q_1$ and $Q_2$ are as defined above; and Z is a Group I element.

According to yet another aspect of the present invention, there is provided a process of preparing a bridged metallocene compound represented by Formula 5 below, the process including:

a) reacting a compound of Formula 10 below with a compound of Formula 2 below treated with a lithium salt or a Grignard reagent;

b) reacting the reaction product of a) with a compound of Formula 7 below and then with $R_6$—Y, followed by acid treatment, to prepare a compound of Formula 11 below; and c) treating the compound of Formula 11 with $4R_7Li$ and reacting the reaction product with a Group IV metal-containing salt:

(2)

(10)

(7)

(11)

-continued (5)

wherein $R_1$, $R_2$, $R_3$, $R_4$, $R_5$, X, Z, M, $Q_1$, and $Q_2$ are as defined above; $R_6$ is an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 740 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical; $R_7$ is a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 740 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical; and Y is a halogen atom.

According to a further aspect of the present invention, there is provided a process of preparing polyolefin, the process including polymerizing olefin using the bridged metallocene compound of Formula 1 as a catalyst.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

In a bridged metallocene compound of Formula 1 according to the present invention, only one cyclopentadienyl group is substituted by a substituent and the substituted position is the alpha position with respect to the bridge. When used as a catalyst for synthesis of polyolefin, a metallocene compound having unsubstituted cyclopentadienyl groups has the smallest steric hindrance. As described above, however, the metallocene compound having unsubstituted cyclopentadienyl groups exhibits low copolymerization activity. In this regard, the substitution of only the alpha position of one cyclopentadienyl group with a substituent acting as an electron donor can increase copolymerization activity, and at the same time, no substitution of the other cyclopentadienyl group can minimize steric hindrance. The metallocene compound according to the present invention is particularly suitable for copolymerization of ethylene and alpha-olefin such as 1-hexene or 1-octene by optimal combination of an electron effect and a steric hindrance effect. Here, the monomers are incorporated and grow into a polymer at the beta positions with respect to the bridge.

The metallocene compound according to the present invention may be a compound represented by Formula 5 or 9 below:

(5)

(9)

wherein $R_1$, $R_2$, $R_3$, $R_4$, M, $Q_1$ and $Q_2$ are as defined in Formula 1.

According to an embodiment of the present invention, the bridged metallocene compound of Formula 5 may be a compound wherein $R_1$ and $R_2$ are each methyl, $R_3$ is hydrogen, and $R_4$ is alkyl of 1-20 carbon atoms.

According to another embodiment of the present invention, the bridged metallocene compound of Formula 9 may be a compound wherein $R_1$ and $R_2$ are each methyl, and $R_3$ and $R_4$ are the same or different and are alkyl of 1-20 carbon atoms, alkenyl of 2-20 carbon atoms, or aryl of 6-40 carbon atoms.

According to an exemplary embodiment of the present invention, the compound of Formula 5 may be selected from compounds represented by Formulae 16-18 below:

(16)

(17)

(18)

The compound of Formula 5 may be synthesized through Reaction Scheme 1 below:

[Reaction Scheme 1]

wherein $R_1$, $R_2$, $R_3$, $R_4$, M, $Q_1$ and $Q_2$ are as defined in Formula 1; $R_5$ is an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical; and X is a halogen atom.

A compound of Formula 2 used as a starting material in Reaction Scheme 1 may be synthesized through Reaction Scheme 2 below. The compound of Formula 2 reacts with butyllithium to prepare a lithium salt which then reacts with a fulvene compound of Formula 3 in which only the 6-position is substituted by a substituent, followed by acid treatment, to obtain a compound of Formula 4. The compound of Formula 4 is converted to the bridged metallocene compound of Formula 5 by a known method.

At the initial reaction step, the compound of Formula 2 may also be treated with a Grignard reagent instead of butyllithium to obtain a Grignard reactant which then reacts with the fulvene compound of Formula 3.

[Reaction Scheme 2]

wherein $R_1$, $R_2$, $R_3$, $R_4$, $R_5$, M, X, $Q_1$ and $Q_2$ are as defined in Formula 1 and Reaction Scheme 1.

Meanwhile, the compound of Formula 9 may be synthesized through Reaction Scheme 3 below:

[Reaction Scheme 3]

wherein $R_1$, $R_2$, $R_3$, $R_4$, $R_5$, M, X, $Q_1$ and $Q_2$ are as defined in Formula 1 and Reaction Scheme 1, and Z is a Group I element.

The compound of Formula 2 is treated with n-BuLi to obtain a lithium salt. Then, the lithium salt reacts with an equimolar concentration of $R_3R_4SiX_2$ and then with a compound of Formula 7 to obtain a compound of Formula 8. The compound of Formula 8 is converted to the bridged metallocene compound of Formula 9 by a known method. Here, a Grignard reagent may also be used instead of butyllithium.

The compound of Formula 5 may also be synthesized through Reaction Scheme 4 below:

[Reaction Scheme 4]

-continued (5)

wherein $R_1$, $R_2$, $R_3$, $R_4$, $R_5$, M, X, Z, $Q_1$ and $Q_2$ are as defined in Formula 1, Reaction Schemes 1 and 3; $R_6$ is an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical; $R_7$ is a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical; and Y is a halogen atom.

The compound of Formula 2 is treated with n-BuLi and the resultant lithium salt reacts with an equimolar concentration of $R_3C(O)OR_4$ and then with the compound of Formula 7, followed by acid treatment in the presence of $R_6Y$, preferably $CH_3I$, to obtain a compound of Formula 11 which is then treated with $4R_4Li$ to obtain a lithium salt compound. Finally, the lithium salt compound reacts with a metal by a known method to prepare the bridged metallocene compound of Formula 5. Here, a Grignard reagent may also be used instead of n-BuLi.

The bridged metallocene compound of Formula 1 thus synthesized can be used as a catalyst in preparation of polyolefin, together with at least one of compounds represented by Formulae 13-15 below as a cocatalyst.

—[Al($R_8$)—O]$_a$— (13)

wherein each $R_8$ may be the same or different and is a halogen radical, a hydrocarbyl radical of 1-20 carbon atoms, or a halogenated hydrocarbyl radical of 1-20 carbon atoms, and a is an integer equal to or greater than 2.

N($R_8$)$_3$ (14)

wherein N is aluminum or boron, and each $R_8$ may be the same or different and is as defined in Formula 13.

[L-H]$^+$[NE$_4$]$^-$ or [L]$^+$[NE$_4$]$^-$ (15)

wherein L is a Lewis base; H is a hydrogen atom; N is a Group XIII element of the Periodic Table; and each E may be the same or different and is an aryl radical of 6-20 carbon atoms substituted by at least one selected from a halogen radical, a hydrocarbyl radical, an alkoxy radical, or a phenoxy radical of 1-20 carbon atoms.

The compound of Formula 13 may be in a linear, circular, or reticular form, and may be methylaluminoxane, ethylaluminoxane, isobutylaluminoxane, butylaluminoxane, etc.

Examples of the compound of Formula 14 include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, ethyldimethylaluminum, methyidiethylaluminum, triphenylaluminum, tri-p-tolylaluminum, dimethylaluminummethoxide, dimethylaluminumethoxide, trimethylboron, triethylboron, triisobutylboron, tripropylboron, and tributylboron.

Examples of the compound of Formula 15 include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl) boron, trimethylammoniumtetra (p-trifluoromethylphenyl) boron, tributylammoniumtetrapentafluorophenylboron, N,N-diethylamylidiumtetraphenylboron, N,N-diethylanilidiumtetraphenylboron, N,N-diethylanilidiumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra (p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, and triphenylcarboniumtetrapentafluorophenylboron.

An olefin-based monomer that can be polymerized in the presence of the bridged metallocene catalyst and the cocatalyst may be ethylene, alpha-olefin, cyclic olefin, etc. A diene olefin-based monomer, a triene olefin-based monomer, or the like, having two or more double bonds, may also be polymerized. Examples of the monomer include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-itocene, norbornene, norbonadiene, ethylidenenorbornene, phenyl norbornene, vinyl norbornene, dicyclopentadiene, 1,4-butadiene, 1,5-pentadiene, 1,6-hexadiene, styrene, alpha-methylstyrene, divinylbenzene, and 3-chloromethylstyrene. Two or more of these monomers may be used for copolymerization.

The bridged metallocene catalyst according to the present invention has low steric hindrance and good (co)polymerization activity, and thus, exhibits good activity in copolymerization of ethylene and alpha-olefin such as 1-hexene, 1-octene, or norbornene.

Hereinafter, the present invention will be described more specifically with reference to the following Examples. The following Examples are for illustrative purposes and are not intended to limit the scope of the invention.

Reagents and solvents mentioned in the following Examples were used after purifying those commercially purchased from Aldrich and Merck. All the synthesis processes were performed in air and moisture-free conditions to increase reproducibility of the experiments. Meanwhile, the structures of compounds obtained were identified by 400 MHz nuclear magnetic resonance (NMR) spectrum.

EXAMPLE 1

Preparation of butylidene(cyclopentadienylethyl)(1,3-dimethylcyclopentadienyl) zirconium dichloride (16)

(1-1) Preparation of 5-butylidene-cyclopenta-1,3-diene 2.5 eq. (20.47 g, 0.31 mol) of cyclopentadiene and diethylamine (7.44 g, 1.102 mol) were added to butylaldehyde (8.93 g, 0.124 mol). The reactant solution was incubated in 80 ml of methanol and then at room temperature for 2 hours. 15.1 ml of acetic acid was added, and the result was stirred for 10 minutes. The resultant solution was then diluted with 200 ml of pentane and treated with 100 ml of water to remove methanol. To remove residual diethylamine, the resultant solution was washed with 200 ml of 1 N HCl for 30 seconds and neutralized with 200 ml of saturated sodium bicarbonate. An organic layer was washed with a NaCl solution, subjected to solvent removal in a rotary evaporator, and distilled at 40° C., to give 5-butylidene-cyclopenta-1,3-diene (yield: 96%).

(1-2) Preparation of 2-(1-cyclopenta-1,4-dienylbutyl)-1,3-dimethylcyclopenta-1,3-diene 15 ml of diethylether was added to 2-bromo-3-methoxy-1,3-dimethyl-cyclopentene (2 g, 9.75 mmol), and the result was cooled to −30° C. Then, n-butyllithium (2.7 g, 9.75 mmol) was added and the reactant solution was incubated at an elevated temperature for 15 minutes and again cooled to −30° C. Then, 1 eq. (1.3 g) of the 5-butylidene-cyclopenta-1,3-diene prepared in (1-1) was added, and the result was incubated for 3 hours. Then, 15 ml of diethylether and 15 ml of water were added, and the resultant solution was washed with 30 ml of 1 N HCl for 3 minutes and neutralized with 30 ml of an aqueous saturated sodium bicarbonate solution. An organic layer was separated, dried over magnesium sulfate to remove water and then subjected to solvent removal in a rotary evaporator. The resultant residue was purified through silica-based column chromatography (hexane) to give 2-(1-cyclopenta-1,4-dienylbutyl)-1,3-dimethylcyclopenta-1,3-diene (yield: 65%).

(1-3) Preparation of butylidene(cyclopentadienylethyl)(1,3-dimethylcyclopentadienyl) zirconium dichloride

The 2-(1-cyclopenta-1,4-dienylbutyl)-1,3-dimethylcyclopenta-1,3-diene (10.4 g, 47.84 mmol) prepared in (1-2) was dissolved in 60 ml of cold tetrahydrofuran. N-butyllithium (26.52 g, 95.68 mmol) was added using a Schlenk line in a nitrogen atmosphere, and the result was stirred for 12 hours. The resultant solution was maintained under a reduced pressure until ⅓ of the total volume of a solvent was removed. The resultant compound was filtered and washed with hexane, to give a lithium salt compound (yield: 95%).

$^1$H NMR (pyridine-d$_5$): δ 6.23 (s, 4H Cp-H), 5.94 (s, 2H Cp-H), 4.19 (quartet, J=3.6 Hz, 1H, CHCH$_3$), 2.32 (s, 6H CH$_3$)ppm.

The lithium salt compound (3.29 g, 7.9 mmol) obtained above was dissolved in a mixed solvent composed of toluene (66 ml) and tetrahydrofuran (17 ml) (4:1). The reactant solution was incubated with ZrCl$_4$(THF)$_2$ (2.98 g, 7.9 mmol) for 3 hours and a solvent was then removed under a reduced pressure. The resultant product was dissolved in toluene and filtered. Finally, toluene was removed and the residue was washed with pentane to give a solid (yield: 58%).

EXAMPLE 2

Preparation of butylidene(cyclopentadienylethyl)(1,3-dimethylcyclopentadienyl) titanium bis(dimethylamine)

(17)

The 2-(1-cyclopenta-1,4-dienylbutyl)-1,3-dimethylcyclopenta-1,3-diene (10.4 g, 47.84 mmol) prepared in (1-2) of Example 1 was dissolved in 60 ml of cold tetrahydrofuran. N-butyllithium (26.52 g, 95.68 mmol) was added using a Schlenk line in a nitrogen atmosphere, and the result was stirred for 12 hours. The resultant solution was maintained under a reduced pressure until ⅓ of the total volume of a solvent was removed. Then, the resultant compound was filtered and washed with hexane, to give a lithium salt compound (yield: 95%). 3.38 g of the lithium salt compound was dissolved in pyridine and cooled to −30° C. Separately, Ti(NMe$_2$)$_2$Cl$_2$ (1.5 g, 8.7 mmol) was dissolved in toluene and set to the same temperature. Then, the two solutions were incubated for 20 minutes while being rapidly stirred. A solvent was then removed under a reduced pressure. The residue was dissolved in pentane and filtered to give a dimethyl amino group-substituted, titanium-containing bridged metallocene compound.

$^1$H NMR (pyridine-d$_5$): δ 6.33 (s, 1H, Cp-H), 6.32 (s, 1H, Cp-H), 6.14 (d, J=2.8 Hz, 1H, Me$_2$Cp-H), 6.08 (d, J=2.8 Hz, 1H, Me$_2$Cp-H), 5.22 (s, 1H, Cp-H), 5.03 (s, 1H, Cp-H), 3.61

(t, 1H, CHCH$_2$), 2.99 (d, J=8.4Hz, 12H, NCH$_3$), 1.95 (s, 3H, CH$_3$), 1.82 (s, 3H, CH$_3$), 1.47 (quartet, J=7.2H, 3H, CHCH$_3$) ppm.

EXAMPLE 3

Preparation of butylidene(cyclopentadienylethyl)(1,3-dimethylcyclopentadienyl) titanium dichloride

(18)

The dimethyl amino group-substituted, titanium-containing compound prepared in Example 2 was dissolved in 35 ml of pentane. 2 eq. (2.11 ml) of Me$_2$SiCl$_2$ was added and the reactant solution was incubated for 30 minutes until a red color disappeared and a solid was obtained. The solid was taken and dissolved in benzene, and the resultant solution was incubated for 12 hours. A produced solid was filtered with a filter and subjected to solvent removal to give a dichloro-substituted, titanium-containing bridged metallocene compound (yield: 50%).

$^1$H NMR (C$_6$D$_6$): δ 6.77 (quartet, J=2.4 Hz, 1H, Cp-H$^{3 \ or \ 4}$), 6.68 (m, 1H, Cp-H$^{3 \ or \ 4}$), 6.67 (d, J=4 Hz, 1H, Me$_2$Cp-H), 6.64 (d, J=4 Hz, 1H, Me$_2$Cp-H), 5.19 (dd, J=3.2, 2.8 Hz, 1H, Cp-H$^{1 \ or \ 5}$), 5.02 (dd, J=3.2, 2.8 Hz, 1H, Cp-H$^{1 \ or \ 5}$), 3.62 (t, 1H, bridge), 1.74 (s, 3H CH$_3$), 1.59 (s, 3H CH$_3$) ppm.

EXAMPLE 4

Preparation of ethylidene(cyclopentadienylethyl)(1,3-dimethylcyclopentadienyl) zirconium dichloride (19)

Figure 1:
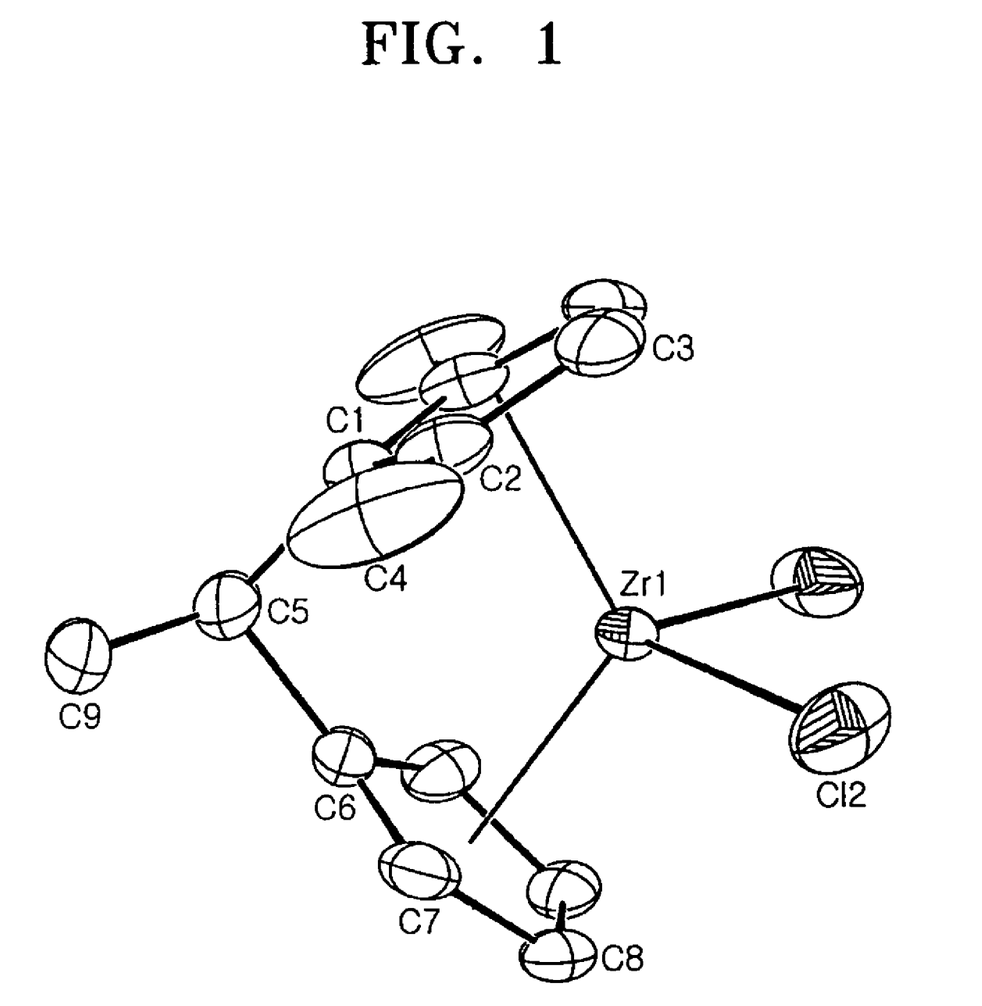
FIG. 1 shows an X-ray crystallographic analysis of a bridged metallocene compound prepared in Example 4.

A zirconium-containing bridged metallocene compound (730 mg, 95%) was prepared in the same manner as in Example 1 except that 1,4,6-trimethylfulvene was used instead of 5-butylidene-cyclopenta-1,3-diene. The molecular structure of the zirconium-containing bridged metallocene compound was identified by X-ray crystallography and the result is shown in FIG. 1

$^1$H and $^{13}$C NMR spectrum 1H NMR (C$_6$D$_6$): δ 6.45-6.40 (m, 1H, Cp-H$^{3 \ or \ 4}$), 6.35-6.33 (m, 1H, Cp-H$^{3 \ or \ 4}$), 6.19 (d, J=3.6 Hz, 1H, Me$_2$Cp-H), 6.16 (d, J=3.6 Hz, 1H, Me$_2$Cp-H), 5.33 (dd, J=4.2, 2.8 Hz, 1H, Cp-H$^{1 \ or \ 5}$), 5.12 (dd, J=4.2, 2.8 Hz, 1 H, Cp-H$^{1 \ or \ 5}$), 3.70 (quartet, J=7.2 Hz, 1H, CHCH$_3$), 1.83 (s, 3H CH$_3$), 1.66 (s, 3H CH$_3$),1.27 (d, J=7.2 Hz, 1H, CHCH$_3$) ppm.

$^{13}$C NMR (C$_6$D$_6$): 124.39 (Cp-CH), 123.31 (Cp-CH), 122.64 (Cp-CH), 121.70 (Cp-CH), 121.15 (Cp-CC), 119.43 (Cp-CC), 118.48 (Cp-CC), 109.17 (Cp-CC), 107.47 (Cp-CH), 105.19 (Cp-CH), 33.12 (bridge-C), 17.41 (CH3), 16.39 (CH3), 14.78 (CH3) ppm.

EXAMPLE 5

Preparation of ethylidene(cyclopentadienylethyl)(1,3-dimethylcyclopentadienyl) titanium dichloride

(20)

Figure 2:
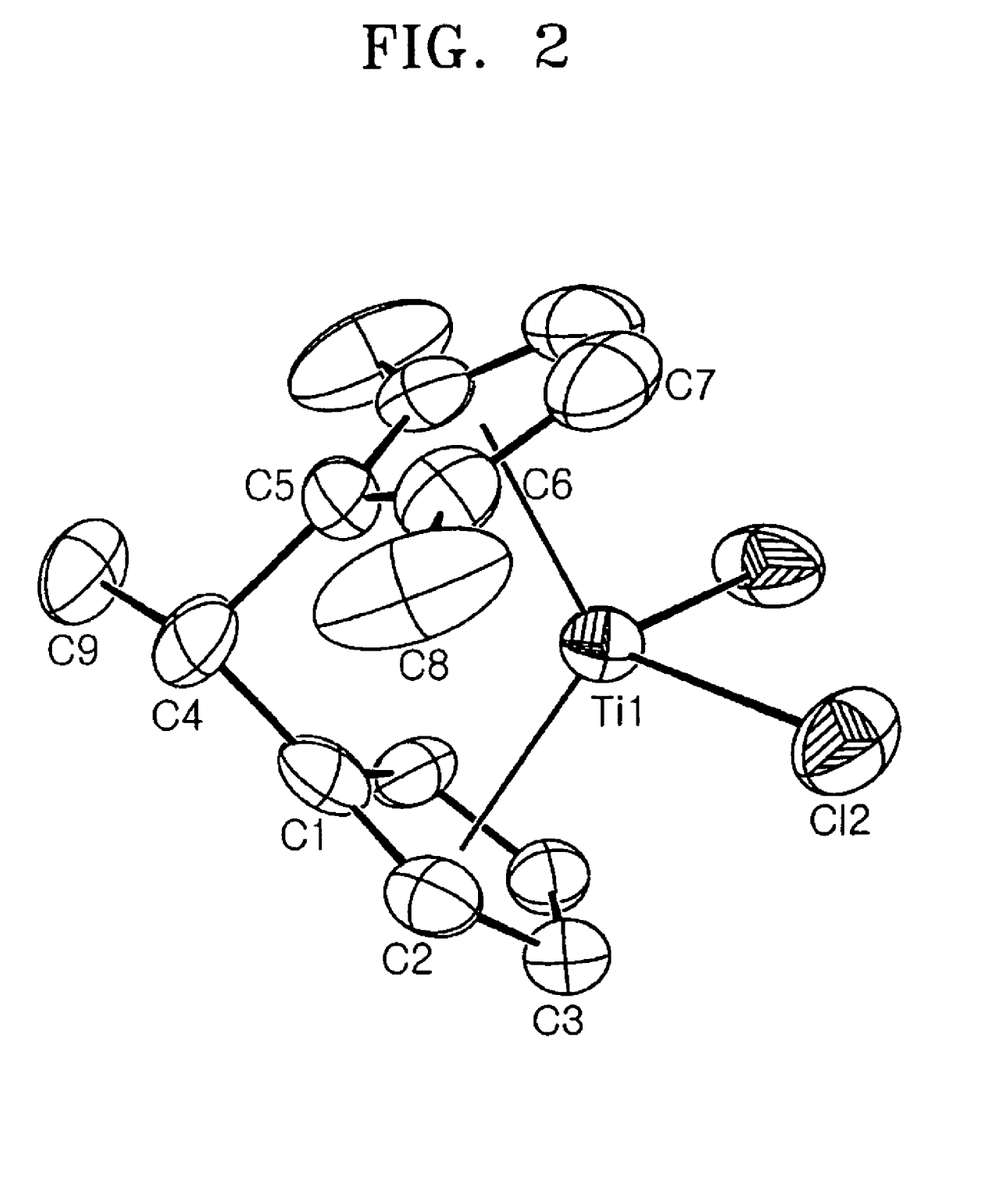
FIG. 2 shows an X-ray crystallographic analysis of a bridged metallocene compound prepared in Example 5.

A titanium-containing bridged metallocene compound was prepared in the same manner as in Example 3 except that 1,4,6-trimethylfulvene was used instead of 5-butylidene-cyclopenta-1,3-diene. The molecular structure of the titanium-containing bridged metallocene compound was determined by X-ray crystallography and the result is shown in FIG. 2.

$^1$H NMR (C$_6$D$_6$: pyridine-d$_5$ (10:1)): δ 6.76 (quartet, J=3 Hz, 1H, Cp-H$^{3 \ or \ 4}$), 6.83 (quartet, J=3 Hz, 1H, Cp-H$^{3 \ or \ 4}$), 6.67 (d, J=3.6 Hz, 1H, Me$_2$Cp-H), 6.64 (d, J=3.6 Hz, 1H, Me$_2$Cp-H), 5.45 (dd, J=3.6, 2.8 Hz, 1H, Cp-H$^{1 \ or \ 5}$), 5.18 (dd, J=3.6, 2.8 Hz, 1H, Cp-H$^{1 \ or \ 5}$), 3.90 (quartet, J=7.2 Hz, 1H, CHCH$_3$), 1.83 (s, 3H CH$_3$), 1.67 (s, 3H CH$_3$), 1.40 (d, J=7.2 Hz, 1H, CHCH$_3$) ppm.

EXAMPLE 6

Preparation of (1,3-dimethyl-cyclopenta-1,3-dienyl)(cyclopenta-1,4-dienyl)-dimethylsilane titanium dichloride (21)

(6-1) Preparation of (1,3-dimethyl-cyclopenta-1,3-dienyl)(cyclopenta-1,4-dienyl)-dimethylsilane 2-bromo-3-methoxy-1,3-dimethyl-cyclopentene (5 g, 24.38 mmol) was dissolved in 30 ml of diethylether and the reactant solution was cooled to −30° C. using a Schlenk line in a nitrogen atmosphere. Then, n-butyllithium (6.67 g) was added and the resultant solution was incubated at an elevated temperature for 15 minutes until a white solid was obtained and then again cooled to −30° C. 1 eq. (3.14 g) of Me$_2$SiCl$_2$ was added and the resultant solution was incubated for 5 hours while gradually being heated to room temperature. Then, NaCp (12.5 ml, 25.0 mmol, 2M in THF) was added to the first reactor preset to −30° C. and the resultant solution was incubated at room temperature for 5 hours or more. 20 ml of water and 20 ml of ethylacetate were added thereto and an aqueous layer was once Washed with 20 ml of ethylacetate and then stirred with 50 ml of 1 N HCl for 3 minutes. The resultant solution was neutralized with 50 ml of a saturated sodium bicarbonate solution, and subjected to solvent removal in a rotary evaporator and then to water removal using magnesium sulfate. Finally, the residue was purified by silica-based column chromatography (hexane), to give (2,5-dimethyl-cyclopenta-1,4-dienyl)(cyclopenta-1,4-dienyl)-dimethylsilane (yield: 66%).

(6-2) Preparation of (1,3-dimethyl-cyclopenta-1,3-dienyl)(cyclopenta-1,4-dienyl)-dimethylsilane titanium dichloride The compound (1.70 g, 7.90 mmol) prepared in (6-1) was dissolved in 20 ml of tetrahydrofuran and the reactant solution was cooled to −78° C. using a Schlenk line in a nitrogen atmosphere. 2 eq. (4.42 g, 15.95 mmol) of n-butyllithium was added, followed by incubation for 12 hours. Then, a white lithium salt was filtered and washed with a small quantity of hexane to give a lithium salt.

$^1$H NMR (pyridine-d$_5$): δ 6.49 (s, 8H, Cp-H), 2.79 (s, 6H, CH$_3$), 1.22 (s, 6H, SiCH$_3$)

The lithium salt (198 mg, 0.87 mmol) and TiCl$_3$(THF)$_3$ (324.2 mg, 0.87 mmol) were placed in a flask. 2.5 ml of −30° C. pyridine was added and the result was incubated for 2 hours. Pyridine was removed under a reduced pressure and PbCl$_2$ (242 mg) was added. The resultant solution was incubated with 2 ml of tetrahydrofuran for 1 hour, subjected to solvent removal under a reduced pressure, and filtered with methylene chloride. Then, methylene chloride was removed and the residue was washed with pentane to give a solid (yield: 52%)

$^1$H NMR(CDCl3): δ 7.05 (s, 6H, Cp-H), 2.23 (s, 6H, CH$_3$), 1.04 (s, 6H, SiCH$_3$)

EXAMPLE 7

Preparation of (1,3-dimethyl-cyclopenta-1,3-dienyl) (cyclopenta-1,4-dienyl)-dimethylsilane zirconium dichloride (22)

The compound (1.70 g, 7.90 mmol) prepared in (6-1) of Example 6 was dissolved in 20 ml of tetrahydrofuran and the reactant solution was cooled to −78° C. using a Schlenk line in a nitrogen atmosphere. Then, 2 eq. (4.42 g, 15.95 mmol) of n-butyllithium was added thereto, and the result was incubated for 12 hours. Then, a white lithium salt was filtered and washed with a small quantity of hexane to give a lithium salt.

$^1$H NMR (pyridine-d$_5$): δ 6.49 (s, 8H, Cp-H), 2.79 (s, 6H, CH$_3$), 1.22 (s, 6H, SiCH$_3$)

The lithium salt (50 mg, 0.22 mmol) and ZrCl$_4$ (49 mg, 0.22 mmol) were placed in a flask. 2 ml of −30° C. pyridine was added thereto, and the result was incubated for 3 hours. Pyridine was removed under a reduced pressure and the resultant product was dissolved in toluene and filtered to remove toluene. The residue was washed with pentane to give a solid (yield: 47%(28 mg)).

EXAMPLE 8

Preparation of ethylidene(cyclopentadienylethyl)(1,3-dimethylcyclopentadienyl) zirconium dichloride (8-1) Preparation of ethylidene (1,3-dimethylcyclopenta-1,3-dienyl)cyclopenta-1,4-diene compound 2-bromo-3-methoxy-1,3-dimethylcyclopentene (4 g, 19.5 mmol) was added to 20 ml of ether in a Schlenk flask under a nitrogen atmosphere. N-butyllithium (5.41 g, 19.5 mmol) was dropwise added with stirring at −30° C., and the result was stirred at room temperature for 30 minutes to obtain a white lithium salt. The lithium salt-containing solution was cooled to −30° C., ethylformate (1.44 g, 19.5 mmol) was dropwise added thereto, and the resultant solution was incubated at room temperature for 1 hour with stirring. Then, NaCp (12.5 ml, 25.0 mmol, 2M in THF) was added to the first reactor preset to −30° C., and the resultant solution was incubated at room temperature for 5 hours or more. Ether was removed under a reduced pressure and 20 ml of dimethylformamide was added. Then, sodium hydride (0.47 g, 19.5 mmol) was added in a nitrogen atmosphere, and the result was stirred for 1 hour. Methyliodide (8.30 g, 58.5 mmol) was dropwise added, and the result was stirred at 30° C. overnight. The resultant solution was extracted with 40 ml of water and 40 ml of hexane, washed with 20 ml of a saline solution three times, subjected to hexane removal, dehydrogenated with 4 ml of ethylacetate and 12 ml of 2N hydrogen chloride, and neutralized with 16 ml of sodium bicarbonate. Finally, water was removed over magnesium sulfate (MgSO$_4$) and a solvent was removed under a reduced pressure, to give the titled compound (yield: 90%).

(8-2) Preparation of Carbon-Bridged Lithium Salt

The compound (2.10 g, 11.25 mmol) obtained in (8-1) was placed in a Schlenk flask. 1.6M methyllithium (14.1 ml, 22.51 mmol) was dropwise added at −78° C. and the reactant solution was incubated at room temperature for two days. The resultant solution was washed with 20 ml of ether and filtered. Ether was removed and the residue was filtered with 20 ml of a mixed solvent of benzene and tetrahydrofuran (1/1) to give a yellow salt coordinated with 1.8 tetrahydrofuran groups (yield: 74%)

$^1$H-NMR(pyridine-$d_5$): δ 6.01 (s, 6H, Cp-H$^{1,2}$), 4.75 (q, J=7.6 Hz, 1H, CH$_3$CH), 2.46 (s, 12H, CH$_3$Cp), 2.02 (d, J=6.8 Hz, 3H, CHCH$_3$) ppm.
$^{13}$C{1H} NMR(pyridine-$d_5$): 122.94, 111.32, 101.27, 67.96, 33.15, 26.04, 24.83, 16.48 ppm.

(8-3) Preparation of ethylidene(cyclopentadienylethyl)(1,3-dimethylcyclopentadienyl) zirconium dichloride The compound (67 g, 0.34 mmol) obtained in (8-2) and ZrCl$_4$(THF)$_2$ (0.13 g, 0.34 mmol) were incubated in 10 ml of pyridine for 12 hours. Then, pyridine was removed under a reduced pressure to obtain a brown tar. The brown tar was solidified with pentane and recrystallized with toluene at −30° C., to give a zirconium-containing, carbon-bridged metallocene compound (yield: 91%).
$^1$H-NMR(benzene-$d_6$): δ 6.25 (dd, J=7.6, 3.6 Hz, 6H, Cp-H), 4.15 (q, J=7.6 Hz, 1H, CH$_3$CH), 2.08 (s, 6H, CH$_3$Cp$^{1\ or\ 4}$), 1.83 (s, 6H, CH$_3$Cp$^{1\ or\ 4}$), 1.56 (d, J=7.6 Hz, 3H, CHCH$_3$)ppm.

COMPARATIVEe EXAMPLE 1

Preparation of ethylenebis(1,4-dimethylcyclopentadienyl)zirconium dichloride 2-bromo-3-methoxy-1,3-dimethylcyclopentene (4 g, 19.5 mmol) was added to 20 ml of ether in a Schlenk flask under a nitrogen atmosphere. N-butyllithium (5.41 g, 19.5 mmol) was dropwise added with stirring at −30° C. and the reactant solution was stirred at room temperature for 30 minutes to obtain a white lithium salt. The white lithium salt-containing solution was cooled to −30° C. and ethylformate (0.72 g, 9.75 mmol) was dropwise added thereto. The resultant solution was stirred at room temperature for 1 hour, ether was removed under a reduced pressure, and 20 ml of dimethylformamide was added. Then, sodium hydride (0.47 g, 19.5 mmol) was added in a nitrogen atmosphere, and the result was stirred for 1 hour. Then, methyl iodide (8.30 g, 58.5 mmol) was dropwise added thereto, and the resultant solution was stirred at 30° C. overnight, extracted with 40 ml of water and 40 ml of hexane, and washed with 20 ml of a saline solution three times. Hexane was removed and the residue was dehydrogenated with 4 ml of ethyl acetate and 12 ml of 2N hydrogen chloride, and neutralized with 16 ml of sodium bicarbonate. Water was removed using magnesium sulfate (MgSO$_4$) and a solvent was removed under a reduced pressure (yield: 90%).

$^1$H-NMR(CDCl$_3$): δ 5.83 (d, J=1.6 Hz, 2H, Cp-H$^3$), 5.03 (s,1H, CH$_3$OCH), 3.33 (d,3H, CH$_3$O), 2.83 (t, J=1.6 Hz, 4H, Cp-H$^4$), 2.04 (s, 6H, CH$_3$Cp), 2.83 (q, J=1.6 Hz, 6H, CH$_3$Cp) ppm. $^{13}$C{1H} NMR(CDCl$_3$): 143.42, 140.30, 136.90, 124.27, 76.08, 56.18, 44.97, 14.97, 14.44 ppm.

The compound (1.48 g, 6.43 mmol) thus obtained was placed in a Schlenk flask. 1.6M methyllithium (14.1 ml, 22.51 mmol) was dropwise added at −78° C. and the reactant solution was incubated with 30 ml of ether at room temperature for two days. The resultant solution was then filtered with washing with 20 ml of ether. Ether was removed and the residue was filtered with 20 ml of a mixed solvent of benzene/tetrahydrofuran (1/1) to obtain a yellow lithium salt coordinated with 1.8 tetrahydrofuran groups (yield: 74%)

$^1$H-NMR(pyridine-$d_5$): δ 6.01 (s, 4H, Cp-H$^{1,2}$), 4.75 (q, J=7.6 Hz, 1H, CH$_3$CH), 2.46 (s, 12H, CH$_3$Cp), 2.02 (d, J=6.8 Hz, 3H, CHCH$_3$) ppm.
$^{13}$C{1H} NMR(pyridine-$d_5$): 122.94, 111.32, 101.27, 67.96, 33.15, 26.04, 24.83, 16.48 ppm.

The obtained lithium salt (0.77 g, 0.34 mmol) and ZrCl$_4$(THF)$_2$ (0.13 g, 0.34 mmol) were incubated with 10 ml of pyridine for 12 hours. Pyridine was removed under a reduced pressure to give a brown tar which was then solidified with pentane. The solid was recrystallized with toluene at −30° C. to give the titled compound (yield: 91%)
$^1$NMR(benzene-$d_6$): δ 6.25 (dd, J=7.6, 3.6 Hz, 4H, Cp-H$^{2,3}$), 4.15 (q, J=7.6 Hz, 1H, CH$_3$CH), 2.08 (s, 6H, CH$_3$Cp$^{1\ or\ 4}$), 1.83 (s, 6H, CH$_3$Cp$^{1\ or\ 4}$), 1.56 (d, J=7.6 Hz, 3H, CHCH$_3$) ppm.

COMPARATIVE EXAMPLE 2

Ethylene polymerization was performed in the same manner in Example 9 as will be described later using a commonly known metallocene catalyst, racemic ethylenebis(indenyl)zirconium dichloride.

EXAMPLE 9

Ethylene Polymerization 30 ml of purified toluene was placed in 70 ml of a glass reactor in a dry box and each catalyst (0.25 mmol) prepared in Examples 3-5 and 7 and MAO (Al/Zr=6000) used as a cocatalyst were added thereto. The glass reactor was sealed and removed from the dry box, and adjusted to 80° C. using a mantle. Polymerization was performed by introducing an ethylene gas at 100 psig. The same procedure was also applied to the catalysts of Comparative Examples 1-2. After the polymerization was terminated, the ethylene gas was quickly released and the glass reactor was washed with acetone. Obtained polymers were filtered to give polyethylene, and the results are presented in Table 1 below.

TABLE 1

| Catalyst | Time (min) | Final Temp. (° C.) | Activity (ton/mol · hr) | Mw | Mw/Mn |
|---|---|---|---|---|---|
| Example 3 | 2 | 87 | 81.6 | Not measured | Not measured |
| Example 4 | 8 | 63 | 15 | 183,000 | 12 |
| Example 5 | 5 | 82 | 100 | 796,000 | 2.4 |
| Example 7 | 2.5 | 110 | 288 | — | — |
| Comparative Example 1 | 8 | 68 | 36 | 68,000 | 4.0 |
| Comparative Example 2 | 5 | 83 | 101 | 383,000 | 1.8 |

As shown in Table 1, the catalysts of Examples 3, 5, and 7 exhibited better ethylene polymerization activity than those of Comparative Examples 1-2. In particular, the catalyst of Example 7 exhibited two times or more activity than that of Comparative Example 2 at the same conditions. The catalysts of Examples 3 and 5 exhibited good activity, and at the same time, the polymers produced using the catalysts also exhibited high molecular weight characteristics.

EXAMPLE 10

Ethylene/Norbornene Copolymerization

A 3.54 M norbornene solution (30 mL) was placed in a glass reactor. A mixture of each catalyst (0.25 mmol) and a cocatalyst, MAO (Al/Zr=4000) was introduced into a syringe. The catalyst/cocatalyst mixture in the syringe was injected into the glass reactor set to 60° C., and polymerization was performed by introducing ethylene at 100 psig. After the polymerization was terminated, the ethylene gas was quickly released and the glass reactor was washed with acetone. Obtained polymers were filtered to obtain ethylene/norbornene copolymers, and the results are presented in Table 2 below.

TABLE 2

| Catalyst | Time (min) | Final Temp. (° C.) | Activity (ton/mol · hr) | Tg (° C.) |
|---|---|---|---|---|
| Example 1 | 5 | 87 | 310 | 186 |
| Example 4 | 5 | 92 | 350 | 177 |
| Example 5 | 10 | 61 | 5.5 | — |
| Comparative Example 1 | 5 | 86 | 182 | 157 |

As shown in Table 2, the catalysts of Examples 1 and 4 using a zirconium metal exhibited better ethylene-norbornene copolymerization activity than the catalyst of Comparative Example 1. This is attributed to less steric hindrance around a cyclopentadienyl ring by which norbornene with large steric hindrance more effectively approaches a metal.

EXAMPLE 11

Ethylene/1-hexene copolymerization

A mixed solution of toluene with 1-hexene of different concentrations (0.1-0.5 M) was placed in a glass reactor. A mixture of the catalyst (0.25 mmol) of Example 3 and MAO (Al/Zr=8000) was introduced into a syringe. The glass reactor was heated to 80° C. and the catalyst/cocatalyst mixture was added thereto. Then, polymerization was performed by introducing ethylene at 60 psig. After the polymerization was terminated, the ethylene gas was quickly released and the glass reactor was washed with acetone. The resultant product was filtered to give an ethylene/1-hexene copolymer, and the results are presented in Table 3 below.

The same polymerization procedure was also performed for the catalyst of Comparative Example 1. However, the polymerization hardly occurred due to very low activity of the catalyst of Comparative Example 1.

TABLE 3

| Conc. of 1-hexene (M) | Temp. (° C.) | Activity (ton/mol · hr) | Tm (° C.) | Mw | Mw/Mn |
|---|---|---|---|---|---|
| 0.1 | 79 | 34.6 | 120 | 537,000 | 2.2 |
| 0.2 | 82 | 36.7 | 107 | 356,000 | 2.3 |
| 0.3 | 82 | 36 | 105 | 281,000 | 2.2 |

TABLE 3-continued

| Conc. of 1-hexene (M) | Temp. (° C.) | Activity (ton/mol · hr) | Tm (° C.) | Mw | Mw/Mn |
|---|---|---|---|---|---|
| 0.4 | 80 | 32 | 106 | 291,000 | 3.2 |
| 0.5 | 79 | 30.9 | 105 | 237,000 | 2.3 |

EXAMPLE 12

Ethylene/1-octene copolymerization

A mixed solution of toluene with 1-octene of different concentrations (0.1, 0.3, and 0.5 M) was placed in a glass reactor, and an appropriate amount of MAO was added thereto. The glass reactor was heated to 90° C., and the catalyst (5 μmol) prepared in Example 3 was added thereto. Polymerization was performed by introducing ethylene at 40 psig. After the polymerization was terminated, the ethylene gas was quickly released and the glass reactor was washed with acetone. The resultant product was filtered to give an ethylene/1-octene copolymer, and the results are presented in Table 4 below.

The same polymerization procedure was also performed using the catalyst of Comparative Example 1. However, the polymerization hardly occurred due to very low activity of the catalyst of Comparative Example 1.

TABLE 4

| Conc. of 1-octene (M) | Temp. (° C.) | Activity (ton/mol · hr) | Mw | Mw/Mn |
|---|---|---|---|---|
| 0.1 | 90 | 6.5 | 108,000 | 3.0 |
| 0.3 | 90 | 2.8 | 69,000 | 2.6 |
| 0.5 | 90 | 3.7 | 55,000 | 2.2 |

What is claimed is:

1. A process of preparing a bridged metallocene compound represented by Formula 5 below, the process comprising:
    a) reacting a compound of Formula 3 below with a compound of Formula 2 below treated with a lithium salt or a Grignard reagent, followed by acid treatment, to prepare a compound of Formula 4 below; and
    b) treating the compound of Formula 4 with a lithium salt and reacting the reaction product with a Group IV metal-containing salt:

(2)

(3)

-continued (4)

(5)

wherein $R_1$ and $R_2$, are each independently a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, provided that $R_1$ and $R_2$ are not hydrogen at the same time, $R_3$ and $R_4$ are a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $R_5$ is an alkyl group of 1-20 carbon atoms, an aryl group of 6-20 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $Q_1$ and $Q_2$ are each independently an alkyl group of 1-20 carbon atoms, an alkenyl group of 2-10 carbon atoms, an alkylaryl group of 7-40 carbon atoms, an arylalkyl group of 7-40 carbon atoms, an aryl group of 6-20 carbon atoms, a substituted or unsubstituted alkylidene group of 1-20 carbon atoms, a substituted or unsubstituted amino group, an alkylalkoxy group of 2-20 carbon atoms, or an arylalkoxy group of 7-40 carbon atoms, M is zirconium, and

X is a halogen atom.

2. A process of preparing a bridged metallocene compound represented by Formula 9 below, the process comprising:

a) reacting a compound of Formula 6 below with a compound of Formula 2 below treated with a lithium salt or a Grignard reagent;

b) reacting the reaction product of a) with a compound of Formula 7 below, followed by acid treatment, to prepare a compound of Formula 8 below; and c) treating the compound of Formula 8 with a lithium salt and reacting the reaction product with a Group IV metal-containing salt:

(2)

(6)

$R_3R_4SiX_2$ (7)

(8)

(9)

wherein $R_1$ and $R_2$ are each independently a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, provided that $R_1$ and $R_2$ are not hydrogen at the same time, $R_3$ and $R_4$ are a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $R_5$ is an alkyl group of 1-20 carbon atoms, an aryl group of 6-20 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $Q_1$ and $Q_2$ are each independently a halogen atom, an alkyl group of 1-20 carbon atoms, an alkenyl group of 2-10 carbon atoms, an alkylaryl group of 7-40 carbon atoms, an arylalkyl group of 7-40 carbon atoms, an aryl group of 6-20 carbon atoms, a substituted or unsubstituted alkylidene group of 1-20 carbon atoms, a substituted or unsubstituted amino group, an alkylalkoxy group of 2-20 carbon atoms, or an arylalkoxy group of 7-40 carbon atoms, M is titanium, X is a halogen atom, and Z is a Group I atom.

3. The process of claim 2, wherein the compound of Formula 2 treated with the lithium salt or the Grignard reagent, the compound of Formula 6, and the compound of Formula 7 have a molar ratio of 1:1:1.

4. A process of preparing a bridged metallocene compound represented by Formula 9 below, the process comprising:

a) reacting a compound of Formula 6 below with a compound of Formula 2 below treated with a lithium salt or a Grignard reagent;

b) reacting the reaction product of a) with a compound of Formula 7 below, followed by acid treatment, to prepare a compound of Formula 8 below; and c) treating the compound of Formula 8 with a lithium salt and reacting the reaction product with a Group IV metal-containing salt:

(2)

(6)

(7)

(8)

(9)

wherein $R_1$ and $R_2$, are each independently a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, provided that $R_1$ and $R_2$ are not hydrogen at the same time, $R_3$ and $R_4$ are a hydrogen atom, an alkyl group of 1-20 carbon atoms, an alkoxy group of 1-10 carbon atoms, an aryl group of 6-20 carbon atoms, an aryloxy group of 6-10 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $R_5$ is an alkyl group of 1-20 carbon atoms, an aryl group of 6-20 carbon atoms, an alkenyl group of 2-20 carbon atoms, an alkylaryl group of 7-40 carbon atoms, an arylalkyl group of 7-40 carbon atoms, an arylalkenyl group of 8-40 carbon atoms, an alkynyl group of 2-10 carbon atoms, or a hydrocarbyl-substituted Group XIV metalloid radical, $Q_1$ and $Q_2$ are each independently a halogen atom, an alkyl group of 1-20 carbon atoms, an alkenyl group of 2-10 carbon atoms, an alkylaryl group of 7-40 carbon atoms, an arylalkyl group of 7-40 carbon atoms, an aryl group of 6-20 carbon atoms, a substituted or unsubstituted alkylidene group of 1-20 carbon atoms, a substituted or unsubstituted amino group, an alkylalkoxy group of 2-20 carbon atoms, or an arylalkoxy group of 7-40 carbon atoms, M is zirconium, X is a halogen atom; and Z is a Group I atom.

* * * * *